United States Patent
Olah

[11] Patent Number: 6,018,088
[45] Date of Patent: Jan. 25, 2000

[54] SUPERACID CATALYZED FORMYLATION-REARRANGEMENT OF SATURATED HYDROCARBONS

[76] Inventor: George A. Olah, 2252 Gloaming Way, Beverly Hills, Calif. 90210

[21] Appl. No.: 09/069,183

[22] Filed: Apr. 29, 1998

Related U.S. Application Data

[60] Provisional application No. 60/046,331, May 7, 1997, and provisional application No. 60/069,100, Dec. 10, 1997.

[51] Int. Cl.⁷ .................................................. C07C 6/08
[52] U.S. Cl. ........................... 585/708; 585/14; 585/709; 585/621; 585/721; 585/724; 585/747; 502/159; 502/168; 502/216; 502/219; 502/224; 502/227; 502/228; 502/305; 502/320
[58] Field of Search .............................. 205/462; 585/14, 585/708, 709, 621, 721, 724, 747; 502/159, 168, 216, 219, 224, 228, 305, 320, 227

[56] References Cited

U.S. PATENT DOCUMENTS

| | | | |
|---|---|---|---|
| 2,037,050 | 4/1936 | Schaarschmidt et al. | 260/134 |
| 2,346,701 | 4/1944 | Pines et al. | 260/488 |
| 2,874,186 | 2/1959 | Friedman | 260/514 |
| 3,356,720 | 12/1967 | Mirviss et al. | 260/533 |
| 3,996,116 | 12/1976 | Herlem et al. | 205/462 |
| 4,433,192 | 2/1984 | Olah | 585/709 |
| 4,472,268 | 9/1984 | Olah | 208/134 |
| 4,508,618 | 4/1985 | Olah | 208/134 |
| 4,547,474 | 10/1985 | Olah | 502/168 |
| 5,073,674 | 12/1991 | Olah | 585/725 |

OTHER PUBLICATIONS

Hart, H. et al., *J. Org. Chem.*, 32, 2669–2673 (1967).

*Primary Examiner*—James O. Wilson
*Attorney, Agent, or Firm*—Pennie & Edmonds LLP

[57] ABSTRACT

A method is disclosed for producing branched aliphatic ketones in hydrocarbon mixtures from isoalkanes by a superacid catalyzed formylation-rearrangement reaction. The method can be used to simultaneously isomerize, if necessary, and formylate hydrocarbons in complex hydrocarbon mixtures such as refinery streams, alkylate mixtures, and natural gas liquids. Natural gas liquids of low octane number are upgraded and oxygenated by adding to the natural gas liquids or reactively producing in the liquids branched aliphatic ketones.

25 Claims, No Drawings

SUPERACID CATALYZED FORMYLATION-REARRANGEMENT OF SATURATED HYDROCARBONS

CROSS-REFERENCE TO RELATED APPLICATIONS

This application claims the benefit of Provisional Application No. 60/046,336, filed May 7, 1997, and Provisional Application No. 60/069,100, filed Dec. 10, 1997.

FIELD OF THE INVENTION

The present invention relates to methods of formylating hydrocarbons to form ketones. In particular, the invention relates to methods of forming branched aliphatic ketones from isoalkanes, and methods of oxygenating and increasing the octane number of hydrocarbon mixtures by converting isoalkanes in the mixtures to branched aliphatic ketones.

BACKGROUND OF THE INVENTION

Oxygenated compounds, such as various alcohols and ethers, have gained widespread application as gasoline additives. Such compounds provide a source of oxygen in the fuel to promote more complete combustion, thereby reducing emissions of carbon monoxide and various hydrocarbons which survive incomplete combustion.

Alcohols such as methanol and ethanol have long been used as gasoline additives. These alcohols, however, have relatively poor blending synergies with gasoline, and fuel mixtures containing them are frequently prone to undesirable phase separation. This tendency to phase separate requires the use of further additives, such as tert-butyl alcohol (TBA), to inhibit phase separation. Other alcohols, such as isopropyl alcohol (IPA), have also been proposed (see, e.g., U.S. Pat. No. 5,191,129) but are not widely used.

Another oxygenated gasoline additive that has recently come into wide usage is methyl tert-butyl ether (MTBE). In addition to being a source of oxygen, MTBE has a relatively high octane number (105), and thus can increase the octane number of fuels as well as promote their cleaner burning. As a result of its octane-enhancing and oxygenating properties, MTBE has become a large tonnage oxygenate and is used worldwide. However, it is not clear that such widespread use of MTBE should continue, in light of safety and health concerns associated with its use as a gasoline additive. In addition, MTBE and related compounds such as ethyl tert-butyl ether (ETBE) and tert-amyl methyl ether (TAME) are relatively expensive to produce, since they require the use of methyl or ethyl alcohol which are not compounds conventionally produced in refinery processes.

Although alcohols and esters are currently used as oxygenating fuel additives, little or no attention has been focused on the possibility of using ketones as additives. As the present invention discloses, certain ketones can have very high octane numbers as well as favorable mixing properties with gasoline. For example, methyl isopropyl ketone (MIPK) has an octane number of 125. However, although MIPK is a known compound, no efficient, economically feasible preparation of MIPK, or of other branched aliphatic ketones, has previously been disclosed.

MIPK has been prepared in the laboratory by the $AlCl_3$ catalyzed reaction of pivaloyl chloride with carbon monoxide in the presence of isopentane (Balaban and Nenitzescu, J. Liebigs Ann. Chem. 1959, 625, 66). MIPK has also been reported as a minor product in the $AlCl_3$ catalyzed reaction of isobutane with carbon monoxide, which yields primarily pivalic acid and isobutyl tert-butyl ketone. An alternative preparation of MIPK was reported by Hart et al. by reacting isoamylene with trifluoroperacetic acid and boron trifluoride (Hart and Lerner, J. Org. Chem. 1967, 32 2669).

In general, Friedel-Crafts (i.e., aluminum halide) catalyzed conversion of saturated hydrocarbons with carbon monoxide gives complex mixtures of products, containing carboxylic acids and ketones. For example, U.S. Pat. No. 2,346,701 discloses a process of oxygenating propane by reacting it with carbon monoxide in the presence of an anhydrous aluminum halide. The reaction produces a complex and poorly characterized mixture of products, including ketones, aldehydes and carboxylic acids.

U.S. Pat. No. 2,874,186 discloses a process for carboxylating normal paraffins, isoparaffins and naphthenes to produce ketones, acids and esters. The process uses a $BF_3$/HF catalyst to oxygenate saturated hydrocarbons with carbon monoxide to produce mainly carboxylic acid products.

Similarly, U.S. Pat. No. 3,356,720 discloses a process for preparing ketones and carboxylic acids from saturated hydrocarbons using a Friedel-Crafts catalyst and a hydrocarbon substituted carbinyl halide.

These prior efforts to oxygenate aliphatic hydrocarbons make use of the classic Koch-type of acid catalyzed carbonylation chemistry. Koch chemistry is well known and is discussed, for example, in Olah, *Friedel-Crafts and Related Chemistry*, Wiley-Interscience, New York (1963), and Olah & Molnar, *Hydrocarbon Chemistry*, Wiley-Interscience, New York (1995), the disclosures of which are incorporated herein by reference. Products obtained in reacting branched alcohols or olefins with carbon monoxide in strong acids in Koch reactions are predominantly branched carboxylic acids with some by-products, such as secondarily formed oligomers and some carbonyl compounds. Many strong acid and even superacid catalysts, such as $H_2SO_4$, HF, $CF_3SO_3H$, HF—$BF_3$ and HF—$SbF_5$ have found application in Koch chemistry. (For a review, see Olah et al., *Superacids*, Wiley-Interscience, New York, p. 295 (1985).) Branched saturated hydrocarbons were known as early as the 1930's to react with carbon monoxide in the presence of aluminum trichloride or other Friedel-Crafts catalysts, mainly through the work of Hopff and Nenitzescu, respectively. They also react in the presence of protic superacids, such as HF—$BF_3$ (see U.S. Pat. No. 2,874,186) or HF—$SbF_5$ (Paatz & Weisgerber, Chm. Ber. 1967, 100, 984) giving typical Koch-Haaf products: primarily branched carboxylic acids, with some oligomers and ketones formed as by-products. Conventional Koch chemistry, however, fails to selectively and efficiently produce branched aliphatic ketones without significant production of carboxylic acids.

Thus, there is a need for a new type of oxygenated gasoline component which can enhance the octane number of the fuel as well as promote cleaner combustion. Further, there is a need for methods to produce such oxygenated additives which are easily adapted for use in hydrocarbon refinery processes.

SUMMARY OF THE INVENTION

The present invention provides a versatile and selective method of producing branched aliphatic ketones in a variety of hydrocarbon components. These branched aliphatic ketones can be added to or formed in hydrocarbon mixtures to oxygenate the mixture and to increase its octane number. In one aspect, the invention includes a method of formylating isoalkanes by subjecting a mixture of a protic acid, carbon monoxide, and one or more isoalkanes to superacidic conditions, whereby the isoalkane undergoes superacid catalyzed formylation-rearrangement to form branched aliphatic ketones in yields greater than 85%. Suitable isoalkanes typically have about 4 to 18 carbon atoms. The superacidic conditions are produced by the combination of a protic acid, such as HF, HF/FSO$_3$H or HF/CF$_3$SO$_3$H, and a Lewis acid such as BF$_3$, TaF$_5$, NbF$_5$ or SbF$_5$, and the reaction is carried out at temperatures of about 0° C. to about 35° C. and pressures of about 10–200 atm. Lower pressures, in the range of 1–20 atm can be used if an optional metal complexing salt is used.

In another aspect, the invention encompasses superacid catalyzed formylation-rearrangement of isoalkanes which are produced in situ by superacid catalyzed isomerization of straight chain alkanes. Hydrocarbon mixtures such as natural gas liquids can be treated according to the present invention to produce branched aliphatic ketones in the mixture, thereby increasing the octane number of the mixture as well as providing for cleaner burning by increasing the oxygen content. The octane number of natural gas liquids treated in accordance with the methods of the present invention can be upgraded from less than 70 to 90 or greater.

In still another aspect, the present invention encompasses a method of upgrading the octane number of gasoline by adding branched aliphatic ketones thereto.

DETAILED DESCRIPTION OF THE INVENTION

The present invention discloses that branched aliphatic ketones are a highly efficient new class of oxygenated gasoline additives. These compounds increase the octane number of the fuel, and provide for cleaner burning oxygenated fuel mixtures. These branched aliphatic ketones are readily produced in high yields in hydrocarbon mixtures typically present in refineries, without the need for costly separations, and without the production of unwanted carboxylic acids.

The branched aliphatic ketones of the present invention are preferably alkyl, secondary alkyl ketones. These branched aliphatic ketones include, for example, methyl isopropyl ketone (MIPK), methyl isobutyl ketone (MIBK), ethyl isopropyl ketone (EIPK), ethyl isobutyl ketone (EIBK), methyl isoamyl ketone (MIAK) and the like. They are readily and economically prepared by the presently disclosed new superacid catalyzed formylation (hydrocarbonylation)-rearrangement of branched alkanes, alkane-alkene alkylates or natural gas liquids.

A representative, non-limiting member of this new class of oxygenated octane enhancers is methyl isopropyl ketone (MIPK). MIPK has a very high octane number (125) and suitable mixing properties with gasoline. For comparison, methyl-tert-butyl ether (MTBE) has an octane number of 105.

In one embodiment, the present invention encompasses a method for producing branched aliphatic ketones by superacid catalyzed formylation-rearrangement reactions. According to the method of the invention, an aliphatic hydrocarbon is mixed with a protic acid and carbon monoxide, and a Lewis acid catalyst is added to produce superacidic conditions under which the hydrocarbon is formylated to produce the corresponding branched aliphatic ketones.

As noted above, the aliphatic hydrocarbon is preferably a $C_4$ to $C_{18}$ isoalkane. The method is not limited to use with a single, pure isoalkane compound. Indeed, mixtures containing any number of $C_4$ to $C_{18}$ isoalkanes may be used without adversely affecting the production therefrom of branched ketone products. When isoalkanes containing from about 8 to about 18 carbon atoms are used, the product mixture includes shorter chain carbonyl products corresponding to those derived from formylation of $C_4$ to $C_8$ isoalkanes, indicating that concurrent C—C bond cleavage and formylation of the longer chain isoalkanes also occurs.

More generally, the method of the present invention can be applied to a hydrocarbon component containing compounds or mixtures of compounds having up to about 18 carbon atoms. Thus, the term "hydrocarbon component" as used herein means any such compounds or mixtures. Typical hydrocarbon components include isoalkanes having about 4 to about 18 carbon atoms; mixtures of isoalkanes having about 4 to about 18 carbon atoms; petrochemical alkylates; refinery streams of hydrocarbons; and natural gas liquids.

Petrochemical alkylates are hydrocarbon mixtures obtained from the alkylation of alkanes and olefins. These alkylates are described in, for example, in U.S. Pat. No. 5,073,674, the disclosure of which is incorporated herein by reference. By "alkylates" is meant the product mixture of the alkylation reaction of an aliphatic hydrocarbon or mixtures of aliphatic hydrocarbons, with an alkenyl hydrocarbon or mixtures of alkenyl hydrocarbons. The aliphatic hydrocarbon can have 3 to 12 carbon atoms, and optionally can contain an alkyl group of 1 to 4 hydrocarbons. The alkenyl hydrocarbon can have 2 to 12 carbon atoms, and optionally can contain an alkyl group of 1 to 4 hydrocarbons.

Natural gas liquids are a well known hydrocarbon component. (See, e.g., Olah and Molnar, *Hydrocarbon Chemistry* (1995).) These hydrocarbons accompany natural gas and consist mainly of saturated straight chain $C_4$–$C_6$ alkanes, with some $C_7$–$C_8$ and up to 5% cyclic and aromatic hydrocarbons. Generally, they do not contain any olefins. The octane number of natural gas liquids is very low (in the 60 range) and thus they have only low commercial value. They are usually burned for their caloric value. Using the methods of the present invention, however, natural gas liquids can be efficiently and cost-effectively upgraded to produce gasolines having an octane number of 90 or more.

The hydrocarbon component thus can be a complex mixture of compounds, and can include both straight and branched chain hydrocarbons, cyclic hydrocarbons, and aromatic hydrocarbons. As described below, the hydrocarbon component need not initially contain any isoalkanes at all, as isoalkanes can be produced in situ by superacid catalyzed isomerization reactions of straight chain alkanes.

These complex hydrocarbon mixtures can be used in the methods of the present invention without any need for separation. Indeed, a particular advantage of the method of the present invention is that complex hydrocarbon mixtures such as refinery streams of hydrocarbons and natural gas liquids can be simultaneously isomerized and oxygenated.

It is well known that straight chain alkanes such as those in refinery streams and natural gas liquids can be isomerized to increase the content of branched chain alkanes (and thereby increase the octane number) under superacidic conditions. Thus, for example, U.S. Pat. Nos. 4,472,268 and 4,508,618 disclose upgrading natural gas liquids with trifluoromethanesulfonic acid (CF$_3$SO$_3$H) or CF$_3$SO$_3$H in conjunction with hydrofluoric acid and Lewis acid catalysts. When typical compositions of such natural gas liquids from the Odessa, Tex. region are treated as disclosed in the '268 and '618 patents, the hydrocarbons are isomerized and the octane number of the natural gas liquid is increased to about 84–86. When these same natural gas liquids are treated according to the method of the present invention, their octane number of the product mixture is increased to about 86 to 95, and the product mixture contains branched aliphatic ketones in amounts of about 12 to about 23%.

It is believed that the superacidic conditions present in the present method facilitate isomerization of straight chain hydrocarbons, as described in the above two patents, with subsequent formylation of the in-situ formed isoalkanes to produce branched aliphatic ketones. Thus, isomerization and formylation are accomplished in a single process.

Advantageously, more volatile compounds such as isobutane and isopentane inevitably formed in concurrent acid catalyzed isomerization (cleavage) are in-situ transformed to methylisopropyl ketone or other branched ketones; thus, the volatility of the gasoline produced is not increased in the treatment, but significant octane enhancement is achieved. In addition, in the upgrading process of the present invention, carcinogenic aromatic hydrocarbons which are typically present in natural gas liquids in amounts of about 1–5% are converted to saturated branched alkanes via ionic hydrogenation-rearrangement processes and are thereby significantly depleted or completely removed. Consequently, the superacidic natural gas liquid upgrading coupled with superacidic formylation-rearrangement gives directly and in a single operation an oxygenated gasoline having a high octane number and cleaner-burning properties, and which is substantially free of carcinogenic aromatics.

The hydrocarbon component is first combined with a protic acid. The protic acid can be any Bronsted acid which, when combined with an appropriate Lewis acid, forms a superacid. Suitable protic acids include HF, as well as mixtures of HF and $FSO_3H$ ("$HF/FSO_3$") or $CF_3SO_3H$ ("$HF/CF_3SO_3H$"). Suitable Lewis acids are well known to those of skill in the art, and are discussed, for example, in Olah et al., *Superacids* (1985). These acids are of the general formula $MX_n$, where M is a group IIIA, IVB or V element, X is a halide, and n is an integer from 3 to 6. Typical Lewis acids suitable for use in the present invention include, for example, $BF_3$, $TaF_5$, $NbF_5$, $SbF_5$ and mixtures thereof. $SbF_5$, although suitable for use in the present invention, is not preferred, as it may yield a greater amount of undesirable by-products and is used up. In a most preferred embodiment, the protic acid is HF and the Lewis acid is $BF_3$.

The protic acid and the hydrocarbon component may be provided as gasses or as liquids, but preferably they are provided as liquids, for ease in handling. The relative amounts of hydrocarbon component and protic acid should be such that the mole ratio of the isoalkane content in the hydrocarbon component to the protic acid is about 1:3 to about 1:50.

When hydrocarbon components are used which will form isoalkanes in situ, such as refinery streams or natural gas liquids, the relative amounts of hydrocarbon component and protic acid are readily determined according to the amount of isoalkane that will be formed under superacidic conditions. This amount is easily calculated by one of skill in the art, based on the distribution of compounds in the hydrocarbon component, or is readily determined by first conducting a superacid catalyzed isomerization on a test aliquot and measuring the amount of isoalkane produced. (See, e.g., U.S. Pat. Nos. 4,472,268 and 4,508,618.)

Carbon monoxide is provided to the hydrocarbon component/protic acid mixture such that the mole ratio of the isoalkane content in the hydrocarbon component to the carbon monoxide is about 1:2 to about 1:8. The amount of isoalkane component as described above, is considered to include the amount of isoalkane which will form under the superacidic conditions.

The Lewis acid subsequently introduced to provide superacidic conditions. It is important to introduce the Lewis acid only after the other components are present, in order to obtain high yield and selectivity of the reaction. The Lewis acid is added in an amount such that the mole ratio of protic acid to Lewis acid is about 1.1:1 to about 6:1. As the proton affinity of CO is higher than that of the alkane, this allows an active formulating agent to be formed, which then directly formylates the isoalkane.

The superacidic formylation-rearrangement reaction is carried out at a temperature not exceeding 35° C. Preferably, the reaction is carried out at a temperature of about 0° C. to about 35° C. The reaction is carried out under pressure, at pressures of about 10 to about 200 atm.

The reaction product or product mixture can be purified using conventional methods known to one of skill in the art and described in Examples 2 and 3. Excess volatile acid, for example, can be removed by vacuum. The product mixture may also be treated with base to neutralize any unreacted acid. Suitable bases include aqueous as well as non-aqueous bases conventionally used, and are known to one of skill in the art. Preferably, a non-aqueous workup is used.

Optionally, the reaction may be carried out in the presence of a CO complexing agent. When a CO complexing agent is used, the pressure needed to carry out the reaction is considerably reduced, to about 1–20 atm. The CO complexing agent is preferably a metal salt, and such metal salts are well known to those skilled in the art. Examples of suitable metal salts include salts of Ag(I), Cu(I) and various salts of transition metals such as Fe(III), cobalt (III), chromium and others known in the art.

Using the methods of the present invention, readily available isobutane, isopentane, or in general $C_4$ to $C_{18}$ isoalkanes are converted into methyl isopropyl ketone (MIPK), ethyl isopropyl ketone (EIPK), ethyl isobutyl ketone (EIBK), methyl isobutyl ketone (MIBK) or the corresponding higher branched ketones via superacid catalyzed formylation-rearrangement with carbon monoxide. Significantly, and in sharp contrast to the well known acid catalyzed carbonylation reaction of aliphatic hydrocarbons, the Koch reaction, carboxylic acids are generally not formed in the reactions in measurable amounts.

As an illustrative example, when isobutane is reacted under pressure (10–200 atm) with carbon monoxide in superacidic HF—$BF_3$ at temperatures not exceeding 35° C., methyl isopropyl ketone (MIPK) is obtained in yields in excess of 90% and selectivity of more than 95%, with unreacted isobutane easily recycled to allow nearly complete conversion. No pivalic acid, the expected product of an acid catalyzed Koch carbonylation reaction, is observed in the reaction products.

Without wishing to be bound by theory, it is believed that the formylation reaction involves electrophilic formylation of the CH bond of the isoalkane, forming an aldehyde intermediate. Under superacidic conditions, the aldehyde intermediate undergoes superelectrophilic activation and rearranges to form a ketone. For example, the superacid catalyzed formylation reaction of isobutane is believed to proceed via pivalaldehyde, which rearranges to form methyl isopropyl ketone (MIPK), as shown below.

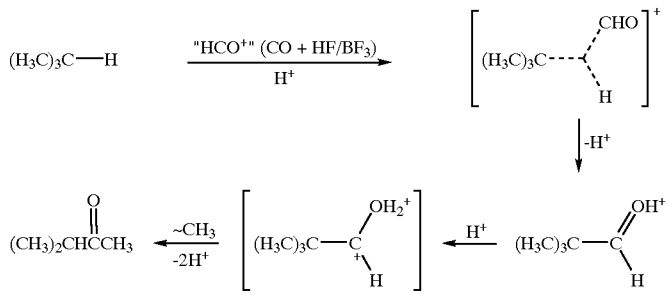

In accordance with this proposed mechanism, it was found that pivalaldehyde itself rearranges quantitatively to MIPK when treated with superacids such as HF, HF—BF$_3$, HF—TaF$_5$, CF$_3$SO$_3$H, FSO$_3$H, HClO$_4$, HF—FSO$_3$H, TeF$_5$OH and the like.

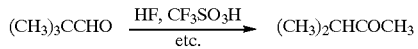

Other isoalkanes containing tertiary CH groups react under superacidic carbonylation conditions in a similar way, giving branched ketones having high octane numbers. Isoalkanes having more than 4 carbon atoms can also isomerize during the reaction, producing a mixture of branched ketone products. For example isopentane is efficiently converted into methyl isobutyl ketone (MIBK) and ethyl isopropyl ketone EIPK. Isohexane gives methyl isoamyl ketone (MIAK) and ethyl isobutyl ketone (EIBK) as major products.

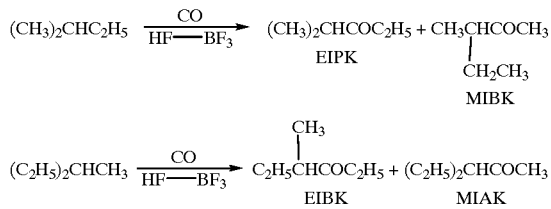

In addition, isoalkanes having more than about 7 carbon atoms can also form shorter chain C$_4$ to C$_8$ branched ketones from concurrent cleavage and isomerization reactions. Carboxylic acids are generally not found in the product mixtures, and any carboxylic acids which might be formed are only minor by-products.

This new superacid catalyzed formylation-rearrangement of isoalkanes is fundamentally different from the Koch-Haaf type of carbonylative carboxylation giving branched carboxylic acids (neoacids). The basis for Koch chemistry producing branched carboxylic acids is the formation of an alkyl cation by the superacid (or related hydride transfer) which then alkylates CO giving an acyl cation and upon aqueous workup the carboxylic acid.

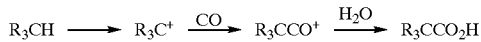

In contrast to the well-known Koch chemistry, the presently disclosed new chemistry giving branched aliphatic ketones to the near exclusion of carboxylic acids can be described as superacid catalyzed formylation-rearrangement. It involves transforming an isoalkane first into the corresponding aldehyde via acid catalyzed electrophilic formylation of the C—H σ bond, and then in situ rearrangement of the aldehydes into branched ketones

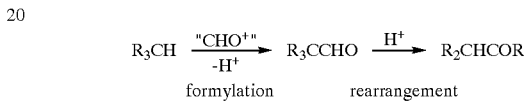

It is believed that the formylation step of the reaction represents electrophilic substitution of a C—H bond, the kind of chemistry which became known only in the 1970's (see, e.g., Olah, *Carbocations and Electrophilic Reactions*, Wiley-Verlag Chemie, 1973; and Olah, *Angew. Chem. Int. Eng. Ed.* 1973, 12, 173). The rearrangement of the intermediate aldehyde to a branched ketone is an example of superelectrophilic activation of carbonyl compounds by acids, allowing them to display carbocationic reactivity (Olah, *Angew. Chem. Int. Eng. Ed.* 1993, 32, 1767).

Certain embodiments and features of the invention are illustrated, and not limited, by the following working examples.

EXAMPLE 1

Formylation-Rearrangement of Isobutane with Non-Aqueous Work-up

A pre-dried autoclave (600 mL, Monel metal) was cooled in a dry ice/acetone bath. HF (56 g, 2.8 mol) and isobutane (20 g, 0.34 mol) were added, and the autoclave was tightly closed and then weighed. Carbon monoxide was then introduced while stirring at 0° C. until a weight increase of 47 g (1.7 mol) was measured. Subsequently, BF$_3$ was slowly introduced at 0° C. with continued stirring until a weight increase of 170 g (2.5 mol) was reached. The pressure at this time at 0° C. was found to be 1500 psi.

The temperature was increased slowly to room temperature and then further to 35° C. The total pressure at this point was 2150 psi. The reaction was continued for a total of 14 hrs, at which time the pressure had dropped by 350 psi, to 1800 psi. Thereafter, the vessel was connected in sequence to two scrubbers kept cooled in an acetone/dry ice bath, and slowly depressurized. The temperature was then slowly raised to 30–35° C. while applying reduced pressure to remove volatile acid. After the bulk of the acid was removed, the vessel was opened and the product treated with non-aqueous base to decompose any remaining formed acid complexes and to neutralize the system. The yield of methyl isopropyl ketone was 90% and the selectivity of the reaction 93%. No pivalic acid was detected in the product; if any acids were formed as by-products, their amounts must be low (<2%).

EXAMPLE 2

Formylation-Rearrangement of Isobutane with Aqueous Work-up

Isobutane was reacted as described in Example 1, up to the point where the reaction vessel was depressurized. After depressurization, the reaction mixture was carefully quenched with 400 g of ice, and neutralized with $NaHCO_3$. Repeated ether extraction and evaporation gave MIPK in slightly less than 90% yield (due to its high solubility in water) with high selectivity. The aqueous workup did not change in any significant way the product distribution, and the aqueous phase did not contain any detectable amount of pivalic acid. No residual isobutane was found (by GC and GCMS analysis) in the product or in the scrubbers, indicating complete conversion.

EXAMPLE 3

Formylation-Rearrangement of Isopentane

Isopentane (2-methylbutane) was reacted as described in Example 1. The product mixture obtained contained methyl isobutyl ketone and ethyl isopropyl ketone in a combined yield of 88%, with complete conversion of isopentane. No carboxylic acid products were identified in the product.

EXAMPLE 4

Formylation-Rearrangement of an Isobutane-Isobutylene Alkylate

A typical alkylate obtained by modified HF catalyzed alkylation of isobutane with isobutylene was reacted as described in Example 1. The alkylate mixture used was obtained from a Texaco refinery, and was substantially in accord with that described in U.S. Pat. No. 5,073,674. The product mixture contained 18% methyl isopropyl ketone and a mixture of isomeric higher branched ketones amounting to a total oxygen incorporation of about 20%. No unreacted isobutane or isobutylene were found.

EXAMPLE 5

Formylation-Rearrangement of Natural Gas Liquid

Odessa (Tex.) region natural gas liquid was reacted under the conditions of Example 1. The natural gas liquid used was substantially in accord with those described in U.S. Pat. Nos. 4,508,618 and 4,472,266. The product mixture contained 12%–23% of branched ketones, including methyl isopropyl ketone, as well as methyl isobutyl ketone, ethyl isopropyl ketone, and some isomeric higher branched ketones. No isobutane or isopentane were detected in the product mixture in any significant amount.

EXAMPLE 6

Isomerization of Pivalaldehyde to Methyl Isopropyl Ketone

To 14.0 g (0.70 mol) of condensed anhydrous HF at −78° C. in a polyolefin flask was added 5.0 mL (0.046 mol) of pivalaldehyde. The flask was tightly closed and stirred with a magnetic stirrer for 2 hours while the temperature was raised to room temperature. After the reaction was completed the reaction mixture was worked up as described in Example 1. The yield of methyl isopropyl ketone was approximately 100%, with no unreacted pivalaldehyde being observed.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed is:

1. A method of preparing branched aliphatic ketones, which comprises: reacting a hydrocarbon component comprising an isoalkane or a mixture of isoalkanes with carbon monoxide in the presence of a superacid comprising a protic acid and a Lewis acid fluoride to catalyze formylation of the isoalkane to thus form a product comprising branched aliphatic ketones.

2. The method of claim 1, wherein the isoalkane has 4 to 18 carbon atoms.

3. The method of claim 1, wherein the protic acid is selected from the group consisting of HF, $HF/FSO_3H$ and $HF/CF_3SO_3H$.

4. The method of claim 1, wherein the Lewis acid fluoride is selected from the group consisting of $BF_3$, $TaF_5$, $NbF_5$, $SbF_5$ and mixtures thereof.

5. The method of claim 1, wherein the isoalkane in the hydrocarbon component and the protic acid are present in the reaction mixture in a mole ratio of from about 1:3 to about 1:50, the isoalkane in the hydrocarbon component and the carbon monoxide are present in the reaction mixture in a mole ratio of from about 1:2 to about 1:8, and the protic acid and Lewis acid fluoride are present in the reaction mixture in a mole ratio of from about 1.1:1 to about 6:1.

6. The method of claim 1, wherein the branched aliphatic ketones are produced in a yield of at least 85% based on the total amount of isoalkane in the hydrocarbon component and the product is substantially free of carboxylic acids.

7. The method of claim 1, wherein the formylation is carried out at a temperature of about 0° C. to about 35° C. and a pressure of about 10 to 200 atm.

8. The method of claim 1, which further comprises carrying out the formylation reaction in the presence of a carbon monoxide complexing metal salt.

9. The method of claim 8, wherein the metal of the complexing metal salt is selected from the group consisting of copper, silver, iron, cobalt and chromium.

10. The method of claim 8, wherein the formylation reaction is carried out at a pressure of about 1 to 20 atm and a temperature of about 0° C. to about 35° C.

11. The method of claim 1, wherein the hydrocarbon component comprises an isoalkane or a mixture of isoalkanes selected from the group consisting of $C_8$ to $C_{18}$ isoalkanes, the formylation is accompanied by concurrent cleavage reactions, and the product comprises $C_5$ to $C_8$ branched saturated ketones.

12. The method of claim 1, wherein the hydrocarbon component comprises the alkylate product of the alkylation reaction of an olefin with an alkane.

13. The method of claim 12, wherein the alkane has 3 to 12 carbon atoms and optionally contains an alkyl group of 1 to 4 carbon atoms, and the olefin has 2 to 12 carbon atoms and optionally contains an alkyl group of 1 to 4 carbon atoms.

14. A method of increasing the octane number of a hydrocarbon component, which comprises: reacting an initial hydrocarbon component comprising straight chain alkanes with carbon monoxide in the presence of a protic acid and a Lewis acid fluoride to produce superacidic conditions in which the straight chain alkanes are isomerized to form isoalkanes, and the isoalkanes thus formed are formylated and subsequently rearranged to form a reaction product comprising branched aliphatic ketones and having an octane number greater than the octane number of the initial hydrocarbon component.

15. The method of claim 14, wherein the protic acid is selected from the group consisting of HF, HF/FSO$_3$H and HF/CF$_3$SO$_3$H, and the Lewis acid fluoride is selected from the group consisting of BF$_3$, TaF$_5$, NbF$_5$, SbF$_5$, and mixtures thereof.

16. The method of claim 14, wherein the protic acid and Lewis acid are present in the reaction mixture in a mole ratio of from about 1.1:1 to about 6:1, and in molar amounts such that the mole ratio of isoalkanes to protic acid is from about 1:3 to about 1:50 and the mole ratio of isoalkanes to carbon monoxide is from about 1:2 to about 1:8, based on the total molar amount of isoalkanes present in the reaction mixture and formed therein by the isomerization of the straight chain alkanes.

17. The method of claim 14, wherein the reaction is carried out at a temperature of about 0° C. to about 35° C. and a pressure of about 10 to 200 atm.

18. The method of claim 14, which further comprises carrying out the formylation reaction in the presence of a carbon monoxide complexing metal salt having a metal selected from the group consisting of copper, silver, iron, cobalt and chromium.

19. The method of claim 18, wherein the formylation reaction is carried out at a pressure of about 1 to 20 atm and a temperature of about 0° C. to about 35° C.

20. The method of claim 14, wherein the hydrocarbon component comprises straight chain alkanes having about 4 to 8 carbon atoms.

21. The method of claim 14, wherein the initial hydrocarbon component comprises natural gas liquids.

22. The method of claim 21, wherein the branched aliphatic ketones are present in the reaction product in an amount of from 5 to 25% by weight.

23. The method of claim 14, wherein the octane number of the initial hydrocarbon component is about 60 to 70 and the octane number of the reaction product is about 90 to 95.

24. A method of increasing the octane number and oxygen content of a hydrocarbon component, which comprises adding thereto from about 1 to about 25% by weight of a branched aliphatic ketone or mixture of branched aliphatic ketones.

25. The method of claim 24, wherein the branched aliphatic ketone has 5 to 19 carbon atoms.

* * * * *